(12) United States Patent
Litvin et al.

(10) Patent No.: US 9,355,502 B2
(45) Date of Patent: May 31, 2016

(54) SYNTHETIC IMAGE GENERATION BY COMBINING IMAGE OF OBJECT UNDER EXAMINATION WITH IMAGE OF TARGET

(71) Applicant: Analogic Corporation, Peabody, MA (US)

(72) Inventors: Andrew Litvin, Stoneham, MA (US); Ram Naidu, Newton, MA (US)

(73) Assignee: Analogic Corporation, Peabody, MA (US)

( * ) Notice: Subject to any disclaimer, the term of this patent is extended or adjusted under 35 U.S.C. 154(b) by 95 days.

(21) Appl. No.: 13/712,153

(22) Filed: Dec. 12, 2012

(65) Prior Publication Data

US 2014/0161333 A1 Jun. 12, 2014

(51) Int. Cl.
| | |
|---|---|
| *G06K 9/00* | (2006.01) |
| *G06T 19/20* | (2011.01) |
| *G01V 5/00* | (2006.01) |
| *G01N 23/04* | (2006.01) |
| *G06T 5/50* | (2006.01) |
| *G06T 11/00* | (2006.01) |

(52) U.S. Cl.
CPC .............. *G06T 19/20* (2013.01); *G01N 23/046* (2013.01); *G01V 5/0008* (2013.01); *G06T 5/50* (2013.01); *G06T 11/008* (2013.01); *G06T 2207/20221* (2013.01); *G06T 2219/2004* (2013.01)

(58) Field of Classification Search
USPC ......... 382/103, 154, 209, 219, 278, 128–133; 348/125, 129, 143, 161
See application file for complete search history.

(56) References Cited

U.S. PATENT DOCUMENTS

| | | | | |
|---|---|---|---|---|
| 7,660,436 | B2* | 2/2010 | Chang et al. | 382/104 |
| 7,738,008 | B1* | 6/2010 | Ball | 348/159 |
| 7,798,907 | B2* | 9/2010 | Piccionelli et al. | 463/49 |
| 7,945,105 | B1* | 5/2011 | Jaenisch | 382/249 |
| 8,320,659 | B2* | 11/2012 | Song et al. | 382/143 |
| 8,369,184 | B2* | 2/2013 | Calhoun | 367/127 |
| 8,541,756 | B1* | 9/2013 | Treas | 250/398 |
| 8,942,411 | B2* | 1/2015 | Yildiz | G06T 7/004 382/100 |
| 2008/0253653 | A1* | 10/2008 | Gable | 382/173 |

OTHER PUBLICATIONS

"Cognitive psychology: Rare targets are often missed in visual search", J.M. Wolfe, T.S. Horowitz and N.M. Kenner, May 26, 2005, Nature, 435, 439-440, 13 pgs.

(Continued)

*Primary Examiner* — Wesley Tucker
(74) *Attorney, Agent, or Firm* — Cooper Legal Group, LLC

(57) ABSTRACT

Among other things, one or more techniques and/or systems for combining a three-dimensional image of a target with a three-dimensional image of an object that is under examination via radiation to generate a three-dimensional synthetic image are provided. Although the target is not actually comprised within the object under examination, the three-dimensional synthetic image is intended to cause the target to appear to be comprised within the object. In one embodiment, one or more artifacts may be intentionally introduced into the three-dimensional synthetic image that are not comprised within the three-dimensional image of the target and/or within the three-dimensional image of the object to generate a synthetic image that more closely approximates in appearance a three-dimensional image that would have been generated from an examination had the target been comprised within the object.

20 Claims, 6 Drawing Sheets

(56) References Cited

OTHER PUBLICATIONS

"Effects of Night Work, Sleep Loss and Time on Task on Simulated Threat Detection Performance", mATHIAS Basner, Joshua Rubinstein, Kenneth M. Fombertein, Matthew C. Coble, Adrian Ecker, Deepa Avinash and David F. Dinges, Sep. 1, 2008, Sleep, vol. 31 No. 9, pp. 1251-1259.

"3-D Threat Image Projection", Yesna O. Yildiz, Douglas Q. Abraham, SOS Agaian and Karen Panetta, 2008, Proceedings of SPIE-IS&T Electronic Imaging, SPIE vol. 6805, 8 pgs.

Wolfe, et al., "Cognitive psychology: Rare targets are often missed in visual search", Nature, 435, 439-440, May 26, 2005.

Basner, et al., "Effects of Night Work, Sleep Loss and Time on Task on Simulated Threat Detection Performance", SLEEP 2008 Sep. 1, 2008, 31(9): pp. 1251-1259.

\* cited by examiner

SYNTHETIC IMAGE GENERATION BY COMBINING IMAGE OF OBJECT UNDER EXAMINATION WITH IMAGE OF TARGET

BACKGROUND

The present application relates to the field of radiation imaging. It finds particular application with computed-tomography (CT) security scanners configured to generate a three-dimensional image of an object under examination. It also relates to medical, security, and other applications where the identification of objects using radiation technology (e.g., x-ray systems, gamma-ray systems, etc.) may be useful.

Radiation systems (e.g., also referred to as imaging systems and/or radiation imaging systems) such as computed tomography (CT) systems, diffraction CT, single-photon emission computed tomography (SPECT) systems, projection systems, and/or line systems, for example, are utilized to provide information, or images, of interior aspects of an object under examination. Generally, the object is exposed to radiation comprising photons (e.g., such as x-ray photons, gamma ray photons, etc.), and an image(s) is formed based upon the radiation absorbed and/or attenuated by interior aspects of the object, or rather an amount of photons that is able to pass through the object. Generally, highly dense aspects of the object absorb and/or attenuate more radiation than less dense aspects, and thus an aspect having a higher density, such as a bone or metal, for example, may be apparent when surrounded by less dense aspects, such as muscle or clothing.

Radiation systems are utilized in a variety of fields to image aspects of an object not readily visible to the naked eye. For example, radiation systems are used in security applications to identify potential threat items, which may include weapons and/or explosives, concealed within a suitcase, bag, person, and/or other object, for example. While automated threat detection systems are available in some radiation systems, often times it is the responsibility of an operator viewing an image of an object to determine whether the object contains a potential threat item (e.g., and thus requires additional inspections, such as a hands-on inspection). Accordingly, operators at security checkpoints and other venues are required to be very attentive. Such attentiveness, combined with the knowledge that few objects actually contain a threat item, may lead to fatigue and/or other distractions that potentially result in an object containing a threat item passing through the system undetected.

SUMMARY

Aspects of the present application address the above matters, and others. According to one aspect, a method for generating a three-dimensional synthetic image representative of an object undergoing an examination and representative of a target is provided. The method comprises acquiring a three-dimensional image of the object undergoing an examination via radiation and acquiring a three-dimensional image of the target, the target not comprised within the object. The method also comprises combining the three-dimensional image of the object with the three-dimensional image of the target to generate the three-dimensional synthetic image whereby the target appears to be comprised within the object. The combining comprises casting artifacts on a portion of the synthetic image representative of at least one of a first aspect of the object proximate the target or the target.

According to another aspect, a method for generating a three-dimensional synthetic image representative of an object undergoing an examination and representative of a target is provided. The method comprises acquiring a three-dimensional image of the object undergoing an examination via radiation and acquiring a three-dimensional image of the target, the target not comprised within the object. The method also comprises determining a desired orientation of the three-dimensional image of the target with respect to the three-dimensional image of the object and determining a desired position of the three-dimensional image of the target with respect to the three-dimensional image of the object. The method also comprises combining the three-dimensional image of the object with the three-dimensional image of the target based upon the desired orientation and the desired position to generate the three-dimensional synthetic image whereby the target appears to be comprised within the object.

According to yet another aspect, an imaging system is provided. The imaging system comprises an examination unit configured to examine an object. The examination unit comprises a radiation source and a detector array. The imaging system also comprises an image generator configured to generate a three-dimensional image of the object based upon an examination of the object. The imaging system further comprises an object location component configured to select a region of the three-dimensional image of the object within which to insert a three-dimensional image of a target, the target not comprised within the object during the examination. The imaging system also comprises an image combining component configured to combine the three-dimensional image of the object with the three-dimensional image of the target to generate a three-dimensional synthetic image whereby the target appears to be comprised within the object.

Those of ordinary skill in the art may appreciate still other aspects of the present application upon reading and understanding the appended description.

FIGURES

The application is illustrated by way of example and not limitation in the figures of the accompanying drawings, in which like references generally indicate like elements and in which.

DETAILED DESCRIPTION

Figure 1:
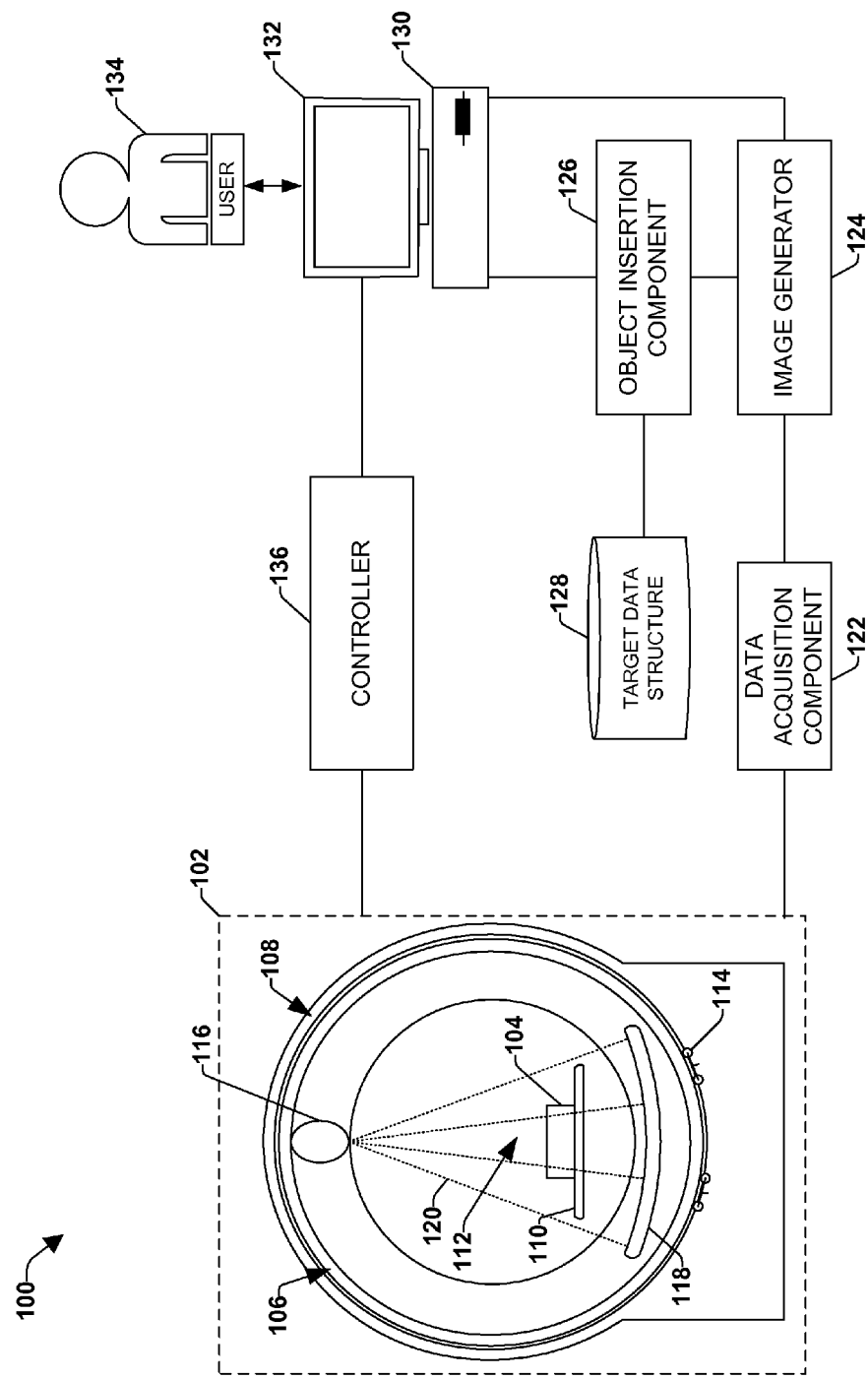
FIG. 1 is a schematic block diagram illustrating an example environment where a radiation system such as described herein may be implemented.

The claimed subject matter is now described with reference to the drawings, wherein like reference numerals are generally used to refer to like elements throughout. In the following description, for purposes of explanation, numerous specific details are set forth in order to provide an understanding of the claimed subject matter. It may be evident, however, that the claimed subject matter may be practiced without these specific details. In other instances, structures and devices are illustrated in block diagram form in order to facilitate describing the claimed subject matter.

X-ray imaging systems and/or other radiation imaging systems are utilized, in one example, for security purposes within transportation networks and/or other sensitive areas by imaging bags, suitcases, people, etc. (e.g., collectively referred to as objects). One example type of such a radiation system is a CT imaging system, which is configured to generate three-dimensional (3D) images of objects under examination and allows for automated and/or manual detection of potential threat items.

In a typical configuration, a CT imaging system presents an operator with two-dimensional (2D) projections and 3D volumetric images of objects in the imaged volume, which may include a bin, bag, or other object conveyed through an examination region. The system may also perform automated detection of threat items, which may highlight suspected threat items. The operator is typically responsible for determining whether an additional inspection, such as a manual inspection, of the object is warranted.

The effectiveness and/or reliability of the operator may depend upon, among other things, training, level of fatigue, and/or presence of performance controls configured to evaluate, control, and/or maintain an operator's performance. Accordingly, a common approach to control and/or maintain operator performance is randomized testing. By way of example, test bags comprising items that appear to be potential threat items may be intermingled with other bags on a conveyor belt for examination by the imaging system, and the operator's ability to correctly identify the test bag as containing a potential threat item may be measured. While such a technique is useful, it may be appreciated that there are a limited number of possible test bags and/or potential threat items at a particular security checkpoint, and thus operators may become familiarized with the test bags and/or potential threat items over time.

Accordingly, systems and/or techniques are described herein that provide for inserting a 3D image of a target (e.g., potential threat item) into a 3D image of an object (e.g., such as a benign suitcase or other bag) to generate a 3D synthetic image. The 3D synthetic image represents both the target and the object, and thus it appears as though the target is comprised within the object (e.g., even though the target was not comprised within the object when the object underwent an examination). A data structure may comprise a plurality (e.g., 10s, 100s, 1000s, etc.) of images, each representative of a different target, and the 3D image that is utilized may be selected at random, for example. Moreover, in one embodiment, the particular object into which the target is artificially inserted may be selected at random. Thus, it may be more difficult for operators to become familiarized with the objects and/or potential threat items, for example.

The 3D synthetic image may be derived by combining a 3D image of the object under examination with a 3D image of the target (e.g., the threat item). By way of example, the 3D image of the object may be analyzed to identify a region of space, substantially free of dense objects, into which the target may be artificially inserted (e.g., thereby reducing visible inconsistencies in the 3D synthetic image). Moreover, artifacts may be rendered in the 3D synthetic image that are neither comprised in the 3D image of the object nor comprised in the 3D image of the target to further reduce a possibility of the operator detecting the presence of image manipulations, for example.

It may be appreciated that while continued reference is made herein to CT systems employed in security applications, the instant disclosure, including the scope of the claims, is not intended to be limited to such embodiments. For example, the systems and/or techniques provided for herein may find applicability in medical applications and/or industrial applications that utilize CT imaging systems and/or other radiation imaging systems to generate images (e.g., such as diffusion systems). By way of example, images of tumors and/or other abnormalities may be inserted into images of patients to test the ability of students, technicians, and/or doctors to identify the abnormalities.

Moreover, that instant application is not intended to be limited to use with a particular radiation measurement technique. For example, the systems and/or techniques described herein may find applicability to charge-integrating imaging systems, photon counting imaging systems, single-energy imaging systems, multi-energy (dual-energy) imaging systems, indirect conversion imaging systems, and/or direct conversion imaging systems, for example.

FIG. 1 illustrates an example environment 100 of a radiation imaging system as provided for herein. It may be appreciated that the example environment 100 merely provides an example arrangement and is not intended to be interpreted in a limiting manner, such as necessarily specifying the location, inclusion, and/or relative position of the components depicted therein. By way of example, the data acquisition component 122 may be part of the detector array 118.

In the example environment 100, an examination unit 102 of the radiation imaging system is configured to examine objects (e.g., bags, suitcases, patients, etc.), such as a first object 104. By way of example, the examination unit may be configured to examine a series of bags placed on a conveyor belt and conveyed through the radiation imaging system.

The examination unit 102 can comprise a rotating gantry 106 and a (stationary) support structure 108 (e.g., which may encase and/or surround at least a portion of the rotating gantry 106 (e.g., as illustrated with an outer, stationary ring, surrounding an outside edge of an inner, rotating ring)). The object 104 can be placed on a support article 110 of the examination unit 102, such as a bed or conveyor belt, for example, and may be conveyed or translated into an examination region 112 (e.g., a hollow bore in the rotating gantry 106) configured to selectively receive the object 104. The rotating gantry 106 can be rotated about the object 104 during the examination and/or moved relative to the object 104 by a rotator 114, such as a motor, drive shaft, chain, roller truck, etc.

The rotating gantry 106 may surround a portion of the examination region 112 and may comprise a radiation source 116 (e.g., an ionizing radiation source such as an x-ray source or gamma-ray source) and a detector array 118 that is mounted on a substantially diametrically opposite side of the rotating gantry 106 relative to the radiation source 116. In this way, the relative position of the radiation source 116 and the detector array 118 (e.g., the position of the radiation source(s) 116 relative to the detector array 118) may be maintained during an examination of the object 104, for example.

During the examination of the object 104, the radiation source 116 emits fan, cone, wedge, and/or other shaped radiation 120 configurations from a focal spot(s) of the radiation source 116 (e.g., a region within the radiation source 116 from which radiation 120 emanates) into the examination region 112. It may be appreciated that such radiation 120 may be emitted substantially continuously and/or may be emitted intermittently or periodically (e.g., a brief pulse of radiation is emitted followed by a resting period during which the radiation source 116 is not activated).

As the emitted radiation 120 traverses the object 104, the radiation 120 may be attenuated differently by different aspects of the object 104. Because different aspects attenuate different percentages of the radiation 120, an image(s) of the object 104 may be generated based upon the attenuation, or variations in the number of photons that are detected by the detector array 118. For example, more dense aspects of the object 104, such as a bone or metal plate, may attenuate more of the radiation 120 (e.g., causing fewer photons to strike the detector array 118) than less dense aspects, such as skin or clothing.

Radiation detected by the detector array 118 may be directly converted and/or indirectly converted into analog signals that can be transmitted from the detector array 118 to a data acquisition component 122 operably coupled to the detector array 118. The analog signal(s) may carry information indicative of the radiation detected by the detector array 118 (e.g., such as an amount of charge measured over a sampling period and/or an energy level of detected radiation), and the data acquisition component 122 may be configured to convert the analog signals into digital signals and/or to compile signals that were transmitted within a predetermined time interval, or measurement interval, using various techniques (e.g., integration, photon counting, etc.).

In the example environment 100, an image generator 124 (e.g., or image reconstructor) is configured to receive the projection data that is output by the data acquisition component 122. Such an image generator 124 may be configured to generate one or more images of the object 104 under examination from the projection data using a suitable analytical, iterative, and/or other image generation technique (e.g., back-projection reconstruction, tomosynthesis reconstruction, iterative reconstruction, etc.). In this way, the data is converted from projection space to image space, a domain that may be more understandable by a user 134 viewing the image(s), for example.

It may be appreciated that because the position of the radiation source 116 and/or the detector array 118 change relative to the object 104 during the examination (e.g., due to the rotation of the radiation source 116 and/or detector array 118 about the object 104), volumetric data indicative of the object 104 may be yielded from the information generated by the detector array 118. Accordingly, the image(s) generated by the image generator 124 may be three-dimensional images (e.g., also referred to as volumetric images), for example. Further, in one embodiment, the image generator 124 may be configured to project the volumetric images to generate two-dimensional images (e.g., also referred to as projections).

The example radiation imaging system further comprises an object insertion component 126 that is operably coupled to the image generator 124 and is configured to insert a 3D image of a target (e.g., an item not comprised within the object 104 undergoing examination) into a 3D image of the object 104 to generate a 3D synthetic image. That is, stated differently, the object insertion component 126 is configured to combine a 3D image of the object 104, provided by the image generator 124, with a 3D image of a target, provided by a target data structure 128, to generate a 3D synthetic image that illustrates the target as comprised within the object 104. By way of example, the object insertion component 126 may be configured to insert a 3D image of a weapon, explosive, or other threat item into a 3D image of a benign bag to create a 3D synthetic image that appears to show a threat item within the bag. In this way, a 3D image may be created that tests the ability of an operator to identify a potential threat item without requiring a test bag, actually containing the threat item, to be examined, for example.

In the illustrated embodiment, 3D images of one or more targets are stored in the target data structure 128, which is operably coupled to the object insertion component 126. In one embodiment, the target data structure 128 may comprise a plurality of 3D images respectively representative of one or more targets (e.g., each representative of a different target), and one or more of the 3D images stored in the target data structure 128 may be selected for insertion into a 3D image of the object 104. It may be appreciated that by having a large pool of 3D images (e.g., respectively representative of a different target), it may be difficult for a user 134 inspecting images to become accustom to the targets (e.g., where becoming accustomed to the targets may make identification of the targets easier and thus decrease the value of the 3D synthetic image as a testing tool or performance measure).

The decision to combine a 3D image of an object undergoing examination with a 3D image of a target may be done randomly and/or according to specified instructions. That is, stated differently, not every 3D image of every object examined may be combined with a 3D image of a target, and the determination of whether to combine a 3D image of an object with a 3D image of a target may be decided at random and/or decided according to predetermined criteria. When an image of an object is not selected for combination with an image of a target, the image of the object may be transmitted directly from the image generator 124 to a terminal 130, for example (e.g., bypassing the object insertion component 126), for example.

The example environment 100 further comprises a terminal 130, or workstation (e.g., a computer), that may be configured to receive images generated by the image generator 124 and/or synthesized images generated by the object insertion component 126. At least some of the received information/images may be provided by the terminal 130 for display on a monitor 132 to a user 134 (e.g., security personnel, medical personnel, etc.). In this way, the user 134 can inspect the image(s) to identify areas of interest within the object 104, for example. The terminal 130 can also be configured to receive user input which can direct operations of the object examination unit 102 (e.g., a speed to rotate, a speed and direction of a support article 118, etc.), for example.

In the example environment 100, a controller 136 is operably coupled to the terminal 130. The controller 136 may be configured to control operations of the examination unit 102, for example. By way of example, in one embodiment, the controller 136 may be configured to receive information from the terminal 130 and to issue instructions to the examination unit 102 indicative of the received information (e.g., adjust a speed of a conveyor belt).

Figure 2:
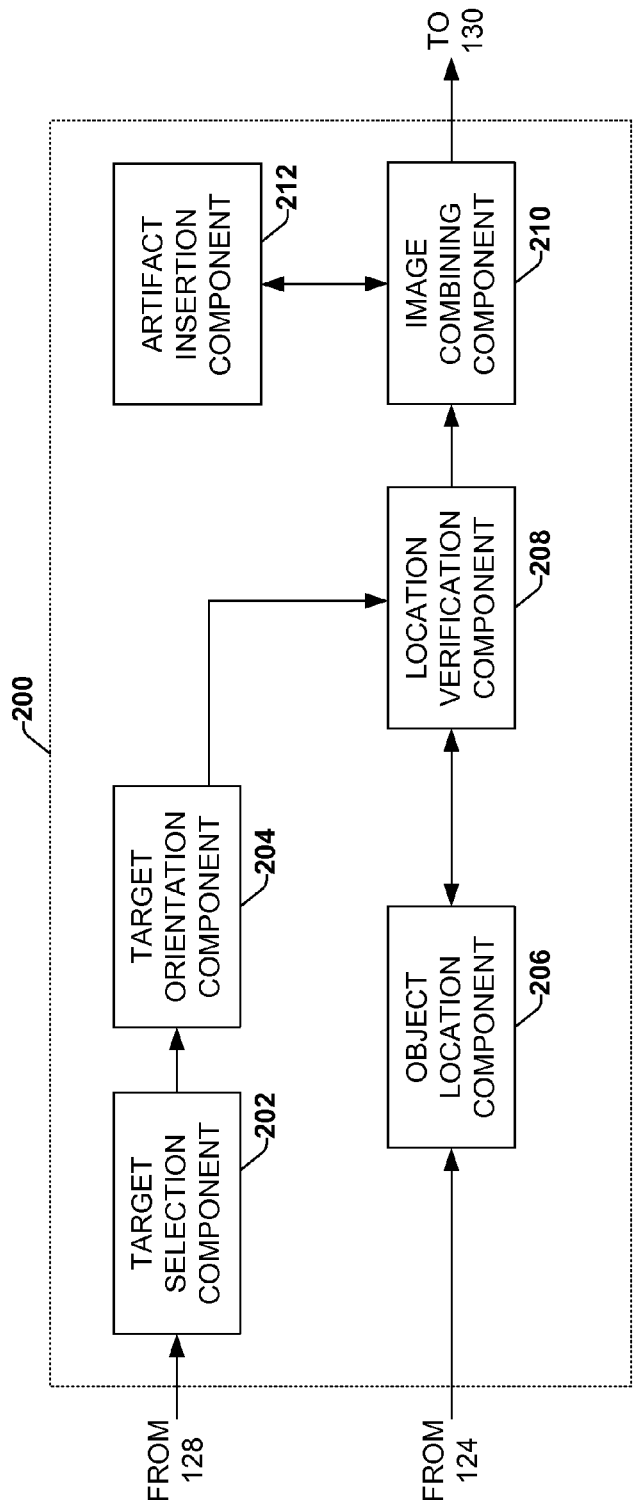
FIG. 2 is a schematic block diagram illustrating an example object insertion component.
Figure 3:
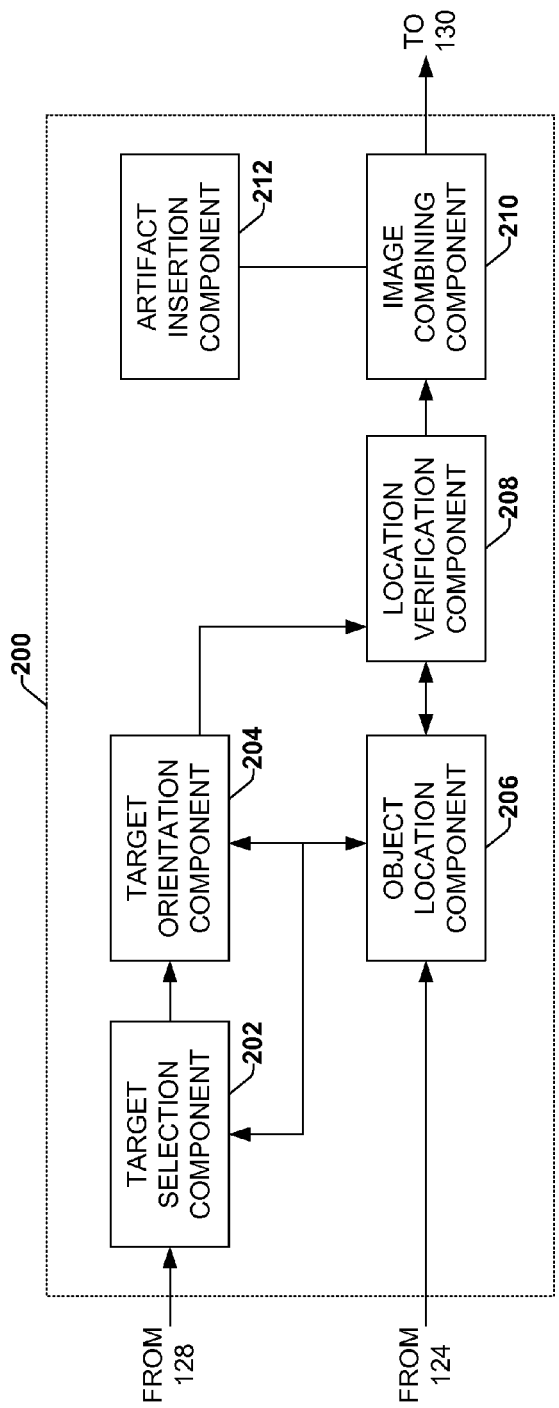
FIG. 3 is a schematic block diagram illustrating an example object insertion component.

FIG. 2-3 illustrate example arrangements for components an object insertion component 200, such as the object insertion component 126 of FIG. 1. It may be appreciated that the components described herein and/or the following arrangements of such components are provided merely as examples.

Thus, the instant disclosure, including the scope of the claims, is not intended to be limited to the following embodiments. That is, the object insertion component 200 may comprise other components configured to perform other functions and/or the components described herein may be arranged in a different arrangement from the arrangements provided for herein.

More particularly, FIG. 2 illustrates an example arrangement of an object insertion component 200 wherein a target and/or an orientation of the target is selected independently of the object under examination. Conversely, FIG. 3 illustrates an example arrangement wherein the orientation of the target and/or the particular target that is artificially inserted into the object may be selected as a function of the object under examination, for example.

Referring now to FIG. 2, the object insertion component 200 may be coupled to an image generator (e.g., 124 in FIG. 1) and a target data structure (e.g., 128 in FIG. 1). The image generator is configured to provide the object insertion component 200 with a 3D image of an object (e.g., 104 in FIG. 1) undergoing examination. The target data structure is configured to provide the object insertion component 200 with a 3D image of a target.

In the illustrated embodiment, the object insertion component 200 comprises a target selection component 202 operably coupled to the target data structure and configured to select a 3D image of a target from the target data structure. The selection of the 3D image of the target by the target selection component 202 may be random or may be a function of specified criteria input into the target selection component 202. For example, based upon a priori knowledge, it may be known that some targets and/or classes of targets are more difficult for operators to detect than other targets. Accordingly, images of targets may be selected by the target selection component 202 based upon a desired degree of difficulty. By way of example, a supervisor of an operator may desire to test the operator on a particular class of target and/or may desire to specify a degree of difficulty at which to test the operator. Based upon input from the supervisor, the target selection component 202 may select a target (or an image of the target) that satisfies the specifications of the supervisor and may retrieve a 3D image of the target from the target data structure, for example.

The example object insertion component 200 also comprises a target orientation component 204 operably coupled to the target selection component 202 and configured to orient the selected 3D image of the target in space. That is, stated differently, the target orientation component 204 may determine a desired orientation of the 3D image of the target relative to defined (fixed) x-, y-, and z-axes. In one embodiment, the defined x-, y-, and z-axes correspond to defined x-, y-, and z-axes of the 3D image of the object. That is, the 3D image of the object may utilize a substantially similar coordinate system as the 3D image of the target, and thus by defining an orientation of the 3D image of the target relative to the coordinate system, an orientation of the 3D image of the target relative to the 3D image of the object may be defined. Accordingly, in such an embodiment, a desired orientation of the target may be defined with respect to the 3D image of the object, for example.

The target orientation component 204 may be configured to randomly select an orientation for the 3D image of the target or may orient the 3D image of the target according to one or more specified parameters. As an example, an instruction may be programmed into the target orientation component 204 that provides for rotating a 3D image of a first target by a specified number of degrees upon each occurrence of a first target being selected for artificial insertion (e.g., or rather upon each occurrence of the 3D image of the first target being selected for combination with a 3D image of an object). Accordingly, the 3D image of the target may be rotated in space (e.g., about any one or more of the axes) by 5 degrees upon a first occurrence and may be rotated in space by another 5 degrees upon a second occurrence, for example.

In one embodiment, the target orientation component 204 may re-orient the 3D image of the target from time-to-time when the 3D image is represented in various 3D synthetic images. By way of example, a 3D image of a first target may be intermittently or periodically reused to test the responsiveness of the operator, for example. If the orientation of the first target appears the same each time the 3D image of the first target is utilized, an operator may become accustom to spotting the target. Accordingly, it may be beneficial to re-orient the 3D image of the first target periodically or intermittently so that the first target does not appear to have the same orientation each time it is represented in a 3D synthetic image. By way of example, a 3D image of the target may be re-oriented in space each time the image is selected by the target selection component 202.

The example object insertion component 200 further comprises an object location component 206 that is operably coupled to the image generator and configured to receive a 3D image of the object under examination. The object location component 206 is configured to determine a desired position of the three-dimensional image of the target with respect to the three-dimensional image of the object. For example, the object location component 206 may be configured to select a region of the 3D image of the object in which to insert the 3D image of the target. In the example embodiment (e.g., where the object location component 206 is not in operable communication with the target selection component 202 and/or the target orientation component 204 and thus has little to no knowledge regarding the selected target), the object location component 206 may be configured to select the region at random and/or to select the region based upon specified criteria (e.g., which does not factor into consideration the selected target). For example, in one embodiment, the object location component 206 selects the region entirely at random without information regarding the density of aspects comprised within the region and/or without information regarding the target.

In another embodiment, the object location component 206 may be configured to select a region of the 3D image of the object based upon density information or other information (e.g., z-effective, Compton score, etc.) derivable from the 3D image of the object. For example, in one embodiment, the object location component 206 is configured identify one or more groups of low-density voxels into which a target could be artificially inserted and to select at least one of the groups as a region into which the 3D image of the target may be inserted.

In still another embodiment, the object location component 206 may be configured to identify one or more boundaries of the object within the 3D image of the object and to select a region within the identified bound(s). By way of example, a 3D image of an object may represent the object as well as areas proximate the object (e.g., such as a bin into which the object is placed while undergoing an examination). Accordingly, the object location component 206 may use analytic, iterative, or other boundary recognition techniques to identify boundaries of the object. After the boundaries are identified, the object location component 206 may select (e.g., at random or based upon information derivable from the 3D image of the object) a region into which to insert the 3D image of the target, for example. In this way, by identifying boundaries of the object prior to selection a region of the 3D image of the object, it may be more certain that the selected region actually represents a portion of the object.

Given that in the example embodiment the object location component 206 may select a region blindly without knowledge regarding the target and/or regarding the orientation of the 3D image of the target, it may be unknown whether the target can be artificially inserted into the selected region (e.g., without there being noticeable mismatch between the target and other objects comprised in the selected region). Accordingly, the object insertion component 200 may comprise a location verification component 208 configured to evaluate whether the 3D image of the target can be combined with the 3D image of the object at the selected region.

The evaluation by the location verification component 208 may take into consideration density, z-effective, and/or other voxel characteristics of respective voxels comprised within the region and/or spatially proximate the region. For example, if dense items and/or items with a high z-effective are represented in the selected region of the 3D image of the object, a 3D synthesized image generated by combining the 3D image of the object with the 3D image of the target in the selected region may comprise visibly cut objects. Accordingly, the location verification component 208 may be configured to utilize analytic, iterative, or other techniques to evaluate one or more metrics on the 3D image of the object and/or the 3D image of the target. By way of example and not limitation, the location verification component 208 may evaluate a cumulative density in the selected region, a number of bright voxels in the selected region, etc.

If the location verification component 208 determines that the 3D image of the target may be combined with the 3D image of the object at the selected region, the 3D image of the object and the 3D image of the target may be transmitted to an image combining component 210 of the object insertion component 200 for image combining. Conversely, if the location verification component 208 determines that the 3D image of the target cannot be combined with the 3D image of the object, the location verification component 208 may notify the object location component 206 to select a different region of the 3D image of the object. Where no region of the 3D image of the object can accommodate the 3D image of the target (e.g., with the particular orientation specified by the target orientation component 204), the location verification component 208 may request that the target orientation component 204 re-orient the 3D image of the target and/or the location verification component 208 may request that the target selection component 202 select a different image of a different target, for example. In still another embodiment, the location verification component 208 may request that the target selection component 202 select a different 3D image and/or may request that the target orientation component 204 re-orient the 3D image of the target without initially requesting that the object location component 206 select a different region.

When the location verification component 208 verifies that the 3D image of the target may be inserted into the selected region of the 3D image of the object, image data of the object and image data of the target may transmitted to the image combining component 210. The image combining component 210 is configured to combine the 3D image of the object with the 3D image of the target at the selected region to generate a 3D synthetic image. For example, the image combining component 210 may be configured to replace image voxels within the selected region of the 3D image of the object with image voxels of the 3D image of the target to generate a 3D synthetic image whereby the target appears to be comprised within the object. In another embodiment, the 3D image of the target may overlay the selected region of the 3D image of the object, for example. In still other embodiments, other techniques for combining and/or fusing the images together are contemplated.

To make the synthetic image more realistic (e.g., more similar to an image that would have been derived had the target actually been comprised within the object), artifacts may be intentionally introduced into the 3D image of the object, the 3D image of the target, and/or the 3D synthetic image. That is, stated differently, image artifacts may be introduced into one or more of the 3D images to simulate artifacts that would have been produced in a 3D image had the target been comprised within the object. For example, if the target was comprised with the object, artifacts may have been cast on a 3D image resulting from the examination in one or more of three different ways: 1) artifacts may have been cast onto aspects of the object, such as a first aspect of the object, as a function of the target; 2) artifacts may have been cast onto the target as a function of aspects of the object, such as a second aspect of the object (e.g., where the first and second aspects may be the same aspect or different aspects); and/or 3) artifacts may have been cast onto at least one of the first aspect of the object and/or the target as a function of a mutual interaction between the target and one or more aspects of the object proximate the target (e.g., which may include the first aspect and/or the second aspect).

To introduce such artifacts into one or more of the 3D images, the example object insertion component 200 comprises an artifact insertion component 212. The artifact insertion component 212 is configured to utilize analytical, iterative, or other artifact approximation techniques to determine where artifacts (e.g., such as metal artifacts) may be cast in the 3D image of the object, the 3D image of the target, and/or the 3D synthetic image. By way of example, in one embodiment, prior to the 3D image of the object being combined with the 3D image of the target, the artifact insertion component 212 may analyze the 3D image of the target to determine how the target may cast artifacts on items/aspects that would be proximate the target and may render such artifacts in the 3D image of the target. Accordingly, when the image combining component 210 combines the 3D image of the target with the 3D image of the object, voxels representing artifacts that would be cast by the target may be combined with corresponding voxels in the 3D image of the object to cause the artifacts cast by the target to be apparent in the 3D synthetic image, for example.

In another embodiment, the artifact insertion component 212 may analyze aspects of the 3D image of the object proximate the selected region to determine how such aspects may cast artifacts in the selected region and may render such artifacts in the 3D image of the object. Accordingly, when the imaging combining component 210 combines the 3D image of the target with the 3D image of the object, voxels representing artifacts that would be cast in the specified region by the aspects of the 3D image proximate the selected region may be combined with corresponding voxels in the 3D image of the object to cause artifacts cast by aspects proximate the specified region to be apparent in the 3D synthetic image, for example.

Further, in still another embodiment, the artifact insertion component 212 may analyze the 3D synthetic image to determine how the mutual interaction of the target with one or more aspects proximate the target may affect how artifacts are cast on the 3D synthetic image and may update properties (e.g., density values, z-effective values, etc.) of one or more voxels based upon the analysis, for example.

In the example embodiment, the 3D synthetic image generated by the image combining component 210 and illustrating the target within the object is output by image combining component 210 to a terminal (e.g., 130 in FIG. 1), where the 3D synthetic image may be displayed to an operator, for example. In this way, the 3D synthetic image may be utilized to test the ability of the operator to identify the target, for example.

FIG. 3 illustrates another example arrangement of the object insertion component 200. Components illustrated in FIG. 3 that are named and/or numbered similarly to the components of FIG. 2 may perform functions similar to those described with respect to FIG. 2. Accordingly, the functions of various components described in FIG. 2 are also applicable to like named/numbered components of FIG. 3 unless otherwise noted.

Like the arrangement illustrated in FIG. 2, the example object insertion component 200 comprises a target selection component 202, a target orientation component 204, an object location component 206, a location verification component 208, an image combining component 210, and an artifact insertion component 212. However, the couplings between such components are different. For example, the arrangement in FIG. 3 provides for operably coupling the object location component 206 to the target selection component 202 and/or the target orientation component 204.

Accordingly, the arrangement illustrated in FIG. 3 may provide for selecting and/or orienting a 3D image of a target as a function of a selected region in the 3D image of the object. By way of example, in one embodiment, the object location component 206 may be configured to select a region in the 3D image of the object (e.g., where the selection may be random and/or as a function of specified criteria) prior to the selection of a target by the target selection component 202. In such an embodiment, the target selection component 202 may be configured to select a target or select a 3D image of a target as a function of the selected region. For example, the target selection component 202 may be configured to measure a size of the selected region and/or estimate a shape of the selected region (e.g., such as via Eigen analysis), and using such information, the target selection component 202 may select a target (or a 3D image of a target) that can be accommodated within the selected region. In another embodiment, the target orientation component 204 may be configured to determine an orientation of the target (or an orientation of the 3D image of the target) based upon the selected region. For example, a 3D image of a target may be unable to fit within the selected region if oriented in a first orientation, but may be accommodated within the selected region if oriented in a second orientation. Accordingly, the target orientation component 204 may, via brute-force (e.g., guess-and-check) and/or other more refined techniques (e.g., such as by finding Eigen vectors within the selected region), determine an orientation for orientating the 3D image of the target as a function of the selected region in the 3D image of the object.

The arrangement in FIG. 3 may also provide for selecting a region of the 3D image of the object as a function of a selected 3D image of a target and/or as a function of how the 3D image of the target is oriented. By way of example, in one embodiment, the target selection component 202 may be configured to select a 3D image of a target and/or the target orientation component 204 may be configured to orient the 3D image of the target prior to a region of the 3D image of the object being selected. Accordingly, the object location component 206 may select the region as a function of the 3D image of the target and/or the orientation of the 3D image of the target. As an example, the object location component 206 may scan the 3D image of the object to identify a smallest region of the image (e.g., having density values below a specified threshold) that can accommodate the 3D image of the object and may select such a region as the region in which to insert the 3D image of the target.

It may be appreciated that although the arrangement of the object insertion component 200 illustrated in FIG. 3 provides for a location verification component 208 configured to verify that the 3D image of the target can be combined with the 3D image of the object at the selected region, such a location verification component 208 may be optional in some embodiments. By way of example, where the 3D image of the target is selected and oriented as a function of the object location component, it may be virtually certain that the selected region can accommodate the target. Accordingly, the location verification component 208 may be unnecessary to verify that the selected region can accommodate the target (e.g., although the location verification component 208 may still be utilized as a final verification tool), for example.

FIGS. 4-9 provide example illustrations of various 3D images at different stages of the image combining process. It may be appreciated that although the images appear to be planar, the images may, in-fact, be three-dimensional images, with the third dimension going into and out of the page.

Figure 4:
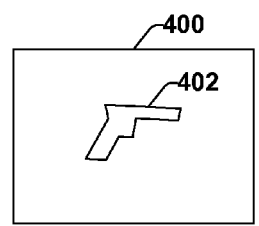
FIG. 4 illustrates an example 3D image of a target such as may be acquired from a target data structure.

With respect to FIG. 4, an example 3D image 400 of a target 402, such as may be retrieved from a target data structure by a target selection component (e.g., 202 in FIG. 2), is illustrated. In the example embodiment, the target 402 is a gun, although other threat items and/or non-threat items are also contemplated. As illustrated, the 3D image 400 may represent more than just the target 402. For example, the 3D image 400 may comprise voxels not representative of the gun, which may be zeroed-out (e.g., such that the voxels are essentially devoid of information and thus represent empty space).

Figure 5:
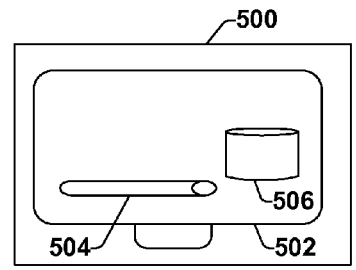
FIG. 5 illustrates an example 3D image of an object such as may be acquired from a radiation examination.

FIG. 5 illustrates an example 3D image 500 of an object 502 (e.g., such as a suitcase) undergoing examination. Such a 3D image 500 may be generated by an image generator (e.g., 124 in FIG. 1) and/or obtained by an object location component (e.g., 206 in FIG. 2), for example. As illustrated, the object 502 is comprised of a first aspect 504, which appears to be substantially rod-shaped, and a second aspect 506, which appears to be substantially cylindrically shaped. It may be appreciated that the object 502 may also be comprised of other objects, such as clothing or other low-attenuation materials, which are not readily discernible in the 3D image 500 of the objet 502, for example. Moreover, it may be appreciated that the 3D image 500 may represent more than just the object 502. For example, the 3D image 500 may also represent region proximate the object 502 at the time the object was examined.

Figure 6:
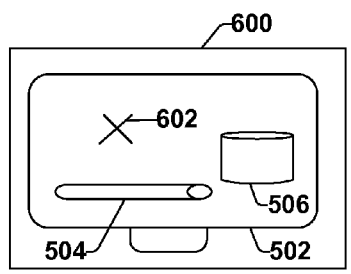
FIG. 6 illustrates an example 3D image of an object upon determining a desired position at which to insert a 3D image of a target.

FIG. 6 illustrates an example 3D image 600 of the object 502 after a desired position of the 3D image 400 of the target 402 has been determine (e.g., and a region within the 3D image 600 has been selected). That is, stated differently, FIG. 6 illustrates an example 3D image 600 that may be output by an object location component (e.g., 206 in FIG. 2) upon the selection of a region in the 3D image 500 of the object 502. The selected region is represented in the 3D image 600 by an "x" 602.

Figure 7:
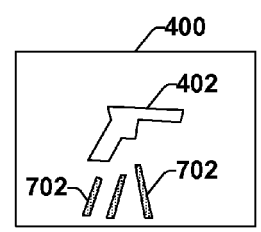
FIG. 7 illustrates an example 3D image of a target, including artifacts which may be cast by the target.
Figure 8:
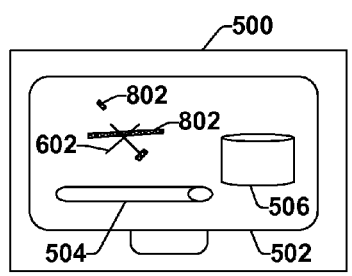
FIG. 8 illustrates an example 3D image of an object, including artifacts which may be cast by one or more aspects of the object.
Figure 9:
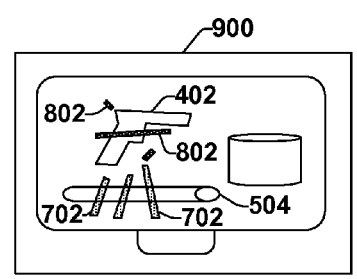
FIG. 9 illustrates an example 3D synthetic image generated from a combination of a 3D image of a target with a 3D image of an object.

FIGS. 7-8 illustrate the intentional introduction of artifacts (e.g., streaks) into the 3D image 400 of the target 402 and into the 3D image 500 of the object 502. That is, stated differently, as described with respect to FIG. 2, it may be desired to intentionally introduce artifacts into one or more of the 3D images to generate a synthetic image that appears to more closely resemble an image that would have been produced had the target been comprised within the object (e.g., where the interactions between the target 402 and aspects of the object 502 may cause artifacts, such as metal artifacts, to appear in a reconstructed image). Accordingly, an artifact insertion component 212 may determine how various aspects of respective images may produce artifacts. For example, as illustrated in FIG. 7, the target 402 may cast artifacts 702 in a region of the 3D image 400 below the target. Moreover, as illustrated in FIG. 8, the first aspect 504 and/or the second aspect 506 of the object 502 may cause artifacts 802 in the selected region of the 3D image 500 of the object 502. Accordingly, when the 3D image 400 of the target 402 is combined with the 3D image 500 of the object 502 to generate a synthetic image 900 as illustrated in FIG. 9, artifacts 702 cast by the target 402 may be rendered on the first aspect 504 of the object 502 because the first aspect 504 is in a location where it was determined that the target 402 would typically cast artifacts (e.g., as illustrated by FIG. 7). Moreover, artifacts 802 cast by the first aspect 504 and/or the second aspect 506 may be rendered on the target 402 because the target 402 is positioned in an area where it was determined that the first aspect 504 and/or the second aspect 506 would typically cast artifacts (e.g., as illustrated by FIG. 8).

Figure 10:
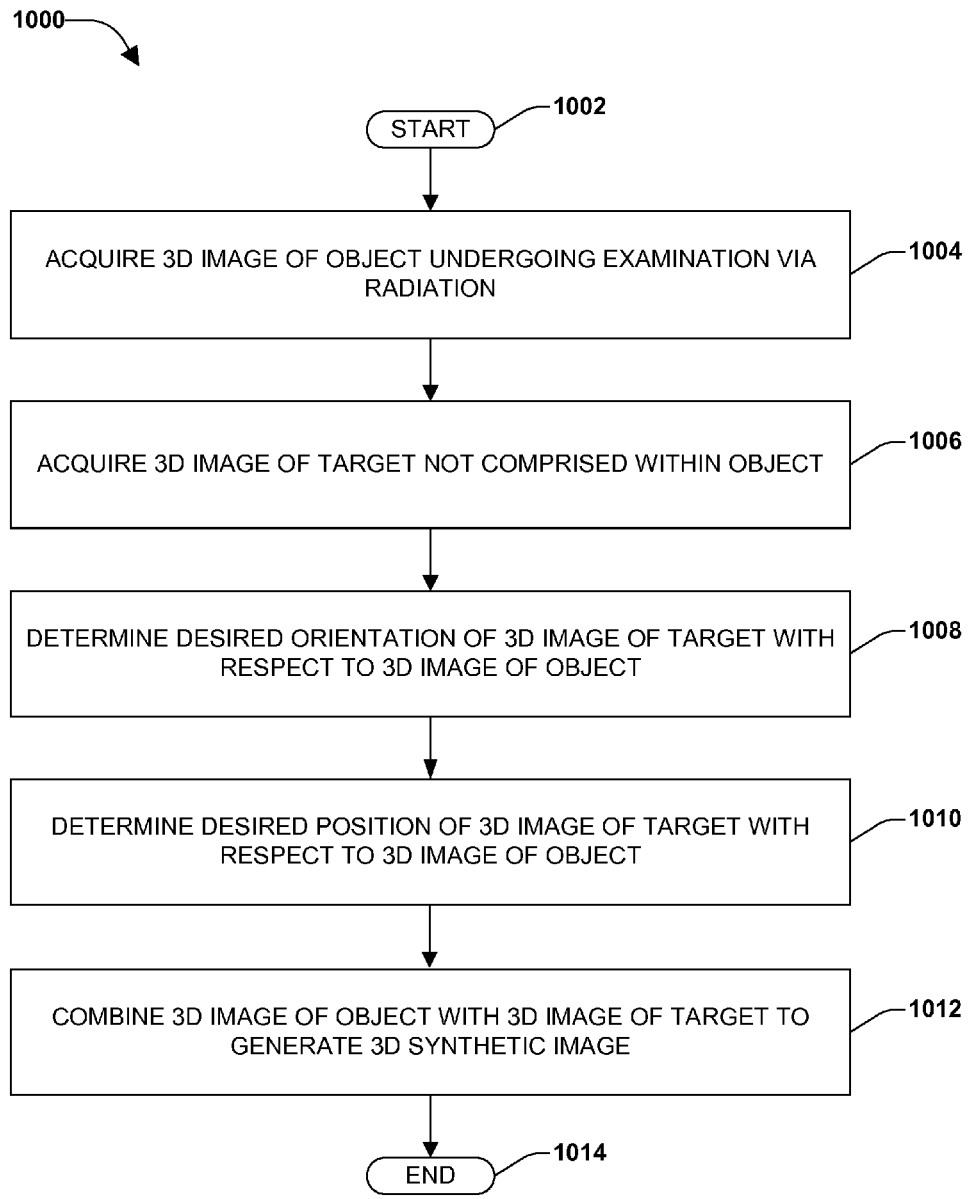
FIG. 10 is a flow chart diagram of an example method for generating a three-dimensional synthetic image representative of an object undergoing examination and representative of a target.

FIG. 10 illustrates an example method 1000 for generating a three-dimensional synthetic image representative of an object undergoing examination and a target. The example method 1000 begins at 1002, and a 3D image of an object undergoing examination via radiation is acquired at 1004. For example, in one embodiment, a computed-tomography (CT) examination or other radiation examination may be performed on the object and the 3D image of the object may be derived from the examination using analytic, iterative, or other reconstruction techniques. The 3D image of the object represents a volume of the object and typically depicts one or more internal aspects of the object. For example, where the object under examination is baggage, the 3D image may illustrate contents of the baggage.

At 1006 in the example method 1000, a 3D image of a target is acquired. The target is an item not comprised within the object, although an end result of the example method 1000 may be to produce an image that appears to illustrate that target as being comprised within the object. Accordingly, the target is an item that is intended to be artificially inserted into the object. By way of example, the target may be a weapon or other threat item that is intended to be artificially inserted into the object to test an ability of an operator to identify the threat item.

As previously described, the selection of a target or 3D image of the target and/or subsequent acquisition of a 3D image of the target at 1006 may be random, may be a function of specified criteria, and/or may be a function of the 3D image of the object acquired at 1004, for example. As an example, in one embodiment, a 3D image of a target is selected and acquired from a pool of 3D images (e.g., respectively representative of different targets) at random. In another embodiment, a user may specify criteria for selecting an appropriate target and/or for selecting a 3D image of a target, for example. In still another embodiment, the 3D image of the object may be scanned to determine where a 3D image of a target may be positioned (e.g., to select a region of the 3D image of the object in which to insert the 3D image of the target). Based upon the determined position or selected region, a target or a 3D image of a target may be selected (e.g., from a group of 3D images respectively representative of one or more targets) that has properties that are desirable for the determined position and/or selected region. For example, a 3D image of the target may be acquired that represents a target that most closely approximates the size and/or shape of the selected region without exceeding the allotted space for the 3D image of the target.

At 1008 in the example method 1000, a desired orientation of the 3D image of the target may be determined with respect to the 3D image of the object. That is, stated differently, an orientation of the 3D image of the target relative to a defined set of x-, y-, and z-axes may be defined. A similar coordinate system may be utilized by the 3D image of the object, and thus by determining an orientation of the 3D image of the target relative to the axes, an orientation of the 3D image of the target relative to the 3D image of the object may be determined.

As previously described, determining a desired orientation of the 3D image of the target may be a random determination, may be a function of specified criteria, and/or may be a function of the desired position of the 3D image of the target with respect to the 3D image of the object. By way of example, a rule may be defined that provides that a 3D image of a target is to be re-oriented by 5 degrees upon respective occurrences of the 3D image being combined with a 3D image of an object. Accordingly, the first time a 3D image of a target is combined with a 3D image of an object, an orientation of the 3D image of the target may be selected at random. Henceforth, each time the 3D image of the target is chosen to be combined with a 3D image of an object, the 3D image of the target may be rotated by another 5 degrees. In another embodiment, the orientation of the 3D image of the target may be at least partially based upon the size and/or shape of a region of the 3D image of the object into which the 3D image of the target is inserted. By way of example, the target may be sized to fit within the selected region if the target is oriented in a first manner, but may not fit within the selected region if the target is oriented in a second manner. Accordingly, the orientation of the 3D image of the target may be chosen as a function of the selected region to facilitate incorporating the target, or the 3D image of the target, within the selected region, for example.

At 1010 in the example method 1000, a desired position of the 3D image of the target with respect to the 3D image of the object is determined. By way of example, a region of the 3D image of the object into which it is desirable to insert the 3D image of the target may be identified/selected. It may be appreciated that although this act is described as occurring after the 3D image of the target has been acquired and after the desired orientation of the 3D image of the target has been determined, in some embodiments, such an act may occur before one or both of these acts. By way of example, as described above, in some embodiments, the acquisition of the 3D image of the target and/or determination regarding an orientation of the 3D image may be a function of the desired position of the 3D image of the target within the 3D image of the object. Accordingly, in such embodiments, it may be desirable to determine a desired position of the 3D image of the target in the 3D image of the object prior to acquiring the 3D image of the target and/or determining a desired orientation of the 3D image of the target.

As previously described with respect to FIG. 2, determining a desired position of the 3D image of the target in the 3D image of the object or selecting a region of the 3D image of the object in which to insert the 3D image of the target may be a random determination, may be a function of specified criteria, and/or may be a function of the acquired 3D image of the target and/or of the desired orientation of the 3D image. By way of example, in one embodiment, the determination may be an arbitrary determination that does not take into consideration the 3D image of the target and/or properties of voxels in the 3D image of the object. In such an embodiment, the determination may be subsequently refined if it is determined that it would be undesired for the 3D image of the target to be inserted at the desired position (e.g., due to mismatch between the target and aspects of the object proximate the desired position), for example. In another embodiment, determining the desired position and/or selecting a region within the 3D image of the object in which to insert the 3D image of the target may comprise identifying a grouping of low-density voxels that is sufficiently large enough to accommodate the target, for example. In still another embodiment, the largest group of voxels below a specified threshold may be selected (e.g., without knowledge of whether such a grouping is sufficient sized to accommodate the 3D image of the target). In still another embodiment, determining the desired position at 1010 may comprise identifying boundaries of the object in the 3D image of the object and merely selecting, from within the bounded area of the 3D image of the object, a region in which to insert the 3D image of the target (e.g., thus ensuring that the 3D image of the target is comprised within the 3D image of the object), for example.

At 1012 in the example method 1000, the 3D image of the target is combined with the 3D image of the object at the desired position or within the selected region to generate a 3D synthetic image whereby the target appears to be comprised within the object. By way of example, voxels of the 3D image of the object within the selected region may be replaced with voxels of the 3D image of the target to artificially insert the target into the object. As another embodiment, the 3D image of the target may be overlaid on top of the 3D image of the object at the desired position (e.g., such that the voxels of the 3D image of the object are hidden or rendered substantially invisible). In yet another embodiment, instead of replacing the voxels of the 3D image of the object, one or more properties of such voxels may be combined with one or more corresponding properties of voxels of the 3D image of the target. For example, density values of one or more voxels of the 3D image of the object may be combined (e.g., summed) with density values of one or more voxels of the 3D image of the target.

It one embodiment, to render the synthetic image more realistic (e.g., such that the synthetic image more closely approximates an image that would have been produced had the target been comprised within the object at the time the object was examination), combining the 3D image of the target with the 3D image of the object may further comprise intentionally or artificially casting artifacts on a portion of the synthetic image representative of a first aspect of the object proximate the target and/or the target itself. By way of example, and not limitation, artifacts may be cast on a portion of the synthetic image representative of the target as a function of a second aspect of the object proximate the target (e.g., where the first aspect and the second aspect may be a same aspect or different aspects). As another example, artifacts may be cast on a portion of the synthetic image representative of the first aspect of the object as a function of the target. As yet another example, artifacts may be cast on a portion of the synthetic image representative of at least one of the first aspect of the object or the target as a function of a mutual interaction between the target and the one or more aspects of the object proximate the target. In this way, the 3D synthetic image may comprise one or more artifacts not comprised in the 3D image of the object and/or not comprised in the 3D image of the target, for example.

The example method 1000 ends at 1014.

Figure 11:
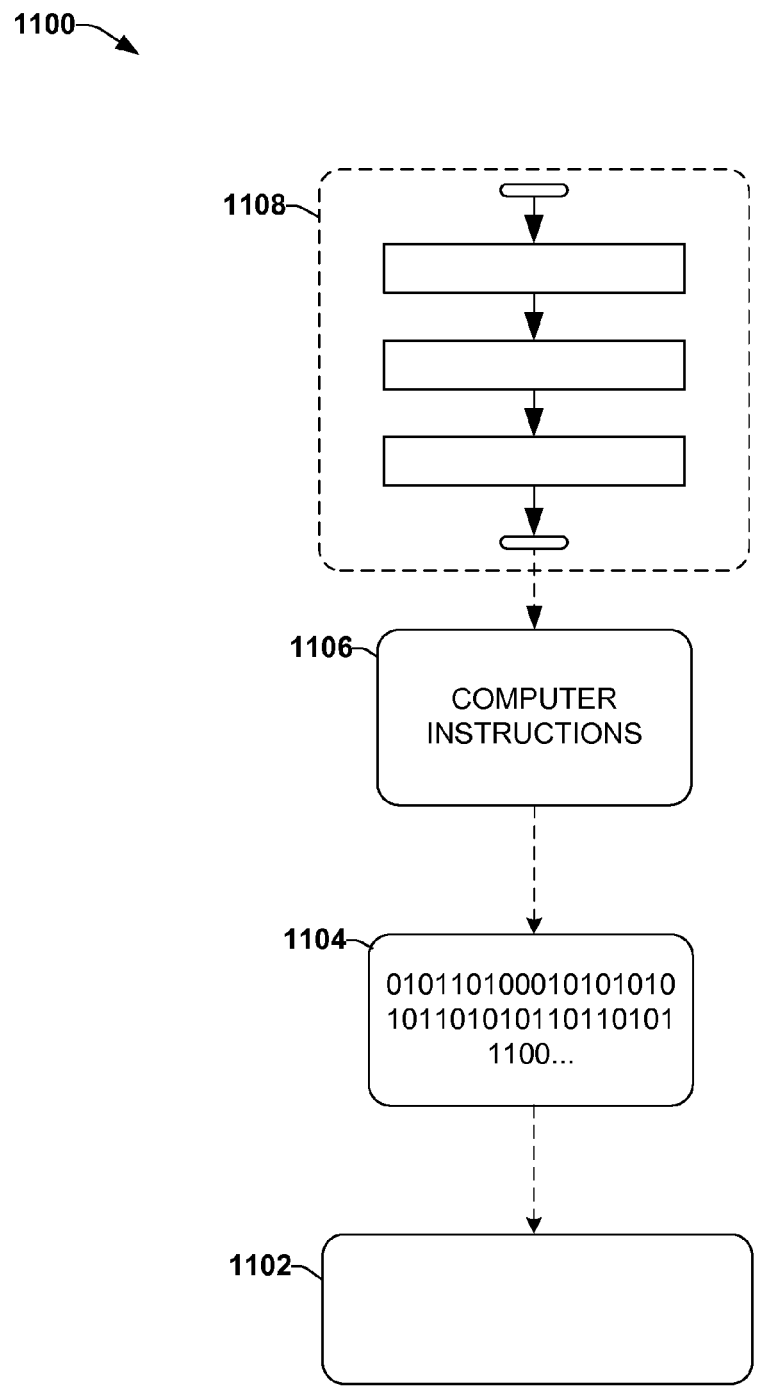
FIG. 11 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 11, wherein the implementation 1100 comprises a computer-readable medium 1102 (e.g., a flash drive, CD-R, DVD-R, application-specific integrated circuit (ASIC), field-programmable gate array (FPGA), a platter of a hard disk drive, etc.), on which is encoded computer-readable data 1104. This computer-readable data 1104 in turn comprises a set of computer instructions 1106 configured to operate according to one or more of the principles set forth herein. In one such embodiment 1100, the processor-executable instructions 1106 may be configured to perform a method 1108, such as at least some of the example method 1000 of FIG. 10, for example. In another such embodiment, the processor-executable instructions 1106 may be configured to implement a system, such as at least some of the exemplary environment 100 of FIG. 1 and/or the exemplary object insertion component 200 of FIG. 2 and/or FIG. 3, for example. Many such computer-readable media may be devised by those of ordinary skill in the art that are configured to operate in accordance with one or more of the techniques presented herein.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used in either the detailed description or the claims, such terms are intended to be inclusive in a manner similar to the term "comprising".

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or identical) channels).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application.

What is claimed is:

1. A method for generating a three-dimensional synthetic image representative of an object undergoing an examination and representative of a target, comprising:
    acquiring a three-dimensional image of the object undergoing an examination via radiation;
    acquiring a three-dimensional image of the target, the target not subject to the examination; and
    combining, in three dimensional image space, the three-dimensional image of the object with the three-dimensional image of the target to generate the three-dimensional synthetic image whereby the target appears to be comprised within the object, the combining comprising casting artifacts on a portion of the three-dimensional synthetic image representative of at least one of:
    a first aspect of the object proximate the target, or
    the target.

2. The method of claim 1, the casting comprising:
    casting artifacts on the portion of the three-dimensional synthetic image representative of the target as a function of a second aspect of the object proximate the target.

3. The method of claim 1, the casting comprising:
    casting artifacts on the portion of the three-dimensional synthetic image representative of the first aspect of the object as a function of the target.

4. The method of claim 1, the casting comprising:
    casting artifacts on the portion of the three-dimensional synthetic image representative of at least one of the first aspect of the object or the target as a function of a mutual interaction between the target and one or more aspects of the object proximate the target.

5. The method of claim 1, comprising:
    determining an orientation of the three-dimensional image of the target; and
    selecting a region of the three-dimensional image of the object within which to insert the three-dimensional image of the target.

6. The method of claim 5, the selecting comprising:
    identifying a grouping of low-density voxels that is sufficiently large enough to accommodate the target.

7. The method of claim 5, the selecting comprising:
    identifying boundaries of the object within the three-dimensional image of the object; and
    identifying, within the boundaries of the object, a grouping of low-density voxels that is sufficiently large enough to accommodate the target.

8. The method of claim 1, comprising:
    selecting a region of the three-dimensional image of the object; and
    selecting, from a group of three-dimensional images respectively representative of one or more targets, the three-dimensional image of the target as a function of the region.

9. The method of claim 1, comprising:
    selecting a region of the three-dimensional image of the object; and
    orienting the three-dimensional image of the target based upon the region.

10. The method of claim 1, the object comprising baggage and the target comprising a threat item.

11. A method for generating a three-dimensional synthetic image representative of an object undergoing an examination and representative of a target, comprising:
    acquiring a three-dimensional image of the object undergoing an examination via radiation;
    acquiring a three-dimensional image of the target, the target not comprised within the object;
    determining a desired orientation of the three-dimensional image of the target with respect to the three-dimensional image of the object;
    determining a desired position of the three-dimensional image of the target with respect to the three-dimensional image of the object; and
    combining, in three-dimensional image space, in three-dimensional image space, the three-dimensional image of the object with the three-dimensional image of the target based upon the desired orientation and the desired position to generate the three-dimensional synthetic image whereby the target appears to be comprised within the object.

12. The method of claim 11, determining the desired position of the three-dimensional image of the target, comprising:
    selecting a region of the three-dimensional image of the object within which to insert the three-dimensional image of the target.

13. The method of claim 12, the selecting comprising:
    identifying a grouping of low-density voxels that is sufficiently large enough to accommodate the target.

14. The method of claim 11, the combining comprising casting artifacts on a portion of the three-dimensional synthetic image representative of at least one of:
    a first aspect of the object proximate the target, or
    the target.

15. The method of claim 14, the casting comprising at least one of:
    casting artifacts on the portion of the three-dimensional synthetic image representative of the target as a function of a second aspect of the object proximate the target;

casting artifacts on the portion of the three-dimensional synthetic image representative of the first aspect of the object as a function of the target; or casting artifacts on the portion of the three-dimensional synthetic image representative of at least one of the first aspect of the object or the target as a function of a mutual interaction between the target and one or more aspects of the object proximate the target.

16. The method of claim 12, the target comprising a threat item.

17. The method of claim 12, comprising:

performing a computed tomography (CT) examination on the object; and deriving the three-dimensional image of the object from the CT examination.

18. The method of claim 12, the three-dimensional synthetic image comprising one or more artifacts not comprised in the three-dimensional image of the object and not comprised in the three-dimensional image of the target.

19. An imaging system, comprising:

an examination unit configured to examine an object, comprising:

a radiation source; and a detector array;

an image generator configured to generate a three-dimensional image of the object based upon an examination of the object;

an object location component configured to select a region of the three-dimensional image of the object within which to insert a three-dimensional image of a target, the target not subject the examination; and an image combining component configured to combine, in three-dimensional image space, the three-dimensional image of the object with the three-dimensional image of the target to generate a three-dimensional synthetic image whereby the target appears to be comprised within the object.

20. The imaging system of claim 19, the three-dimensional synthetic image comprising one or more artifacts not comprised in the three-dimensional image of the object and not comprised in the three-dimensional image of the target.

* * * * *